United States Patent
Farhan

(10) Patent No.: US 7,825,813 B2
(45) Date of Patent: Nov. 2, 2010

(54) IDENTIFYING ACTIVITY IN AN AREA UTILIZING SOUND DETECTION AND COMPARISON

(75) Inventor: Fariborz M. Farhan, Alphretta, GA (US)

(73) Assignee: Intelehealth, Inc, Atlanta, GA (US)

( * ) Notice: Subject to any disclaimer, the term of this patent is extended or adjusted under 35 U.S.C. 154(b) by 243 days.

(21) Appl. No.: 11/828,121

(22) Filed: Jul. 25, 2007

(65) Prior Publication Data

US 2008/0025477 A1    Jan. 31, 2008

(51) Int. Cl.
*G08B 23/00* (2006.01)
(52) U.S. Cl. .............................. 340/573.1; 340/286.07; 340/539.12; 340/539.14; 340/540; 367/198; 381/56; 705/2
(58) Field of Classification Search ............... 340/573.1, 340/575, 539.12–539.22, 286.07, 540; 367/198; 381/56; 705/2; 379/32.01; 128/904
See application file for complete search history.

(56) References Cited

U.S. PATENT DOCUMENTS

| | | | |
|---|---|---|---|
| 4,284,849 A | 8/1981 | Anderson et al. | |
| 4,303,801 A | 12/1981 | Anderson et al. | |
| 5,504,714 A | 4/1996 | Shonting | |
| 5,553,609 A | 9/1996 | Chen et al. | |
| 6,058,076 A | 5/2000 | Komninos | |
| 6,072,392 A | 6/2000 | Henderson et al. | |
| 6,445,298 B1 | 9/2002 | Shepher | |
| 6,696,957 B2 | 2/2004 | Shepher | |
| 7,405,653 B2* | 7/2008 | Tice et al. | 340/539.12 |
| 7,522,035 B2* | 4/2009 | Albert | 340/521 |
| 2001/0044588 A1 | 11/2001 | Mault | |
| 2002/0171551 A1* | 11/2002 | Eshelman et al. | 340/573.1 |
| 2003/0117279 A1 | 6/2003 | Ueno et al. | |
| 2005/0275541 A1 | 12/2005 | Sengupta et al. | |
| 2005/0286686 A1 | 12/2005 | Krstulich | |
| 2006/0017558 A1 | 1/2006 | Albert et al. | |
| 2006/0017561 A1 | 1/2006 | Albert | |
| 2006/0033625 A1* | 2/2006 | Johnson et al. | 340/573.1 |

\* cited by examiner

*Primary Examiner*—Brent Swarthout
(74) *Attorney, Agent, or Firm*—Smith Frohwein Tempel Greenlee Blaha, LLC; Gregory Scott Smith

(57) ABSTRACT

Microprocessor technology is used to detect routine sounds in a substantially enclosed environment to determine normal or abnormal activity or noise within the environment (i.e., habitual behavior of an individual) A device is situated in a substantially enclosed environment with audio input device similar to a microphone and an optional visual display for interaction with the local users. The device has the ability to be controlled locally via key-pad or USB port connected to a local laptop computer, or remotely via a phone line or Ethernet connection to internet. The device further performs audio pattern recognition using waveform matching scheme to detect the occurrence of pre-programmed sounds representing routine activities. The microprocessor counts the number occurrence of each recognizable sound for a particular interval and over a length of a day or other duration and reports to a remote server. The remote server performs tracking and trending analysis to a web-based caregiver client. Significant changes are detected and reported to caregiver or family web-based client.

12 Claims, 5 Drawing Sheets

IDENTIFYING ACTIVITY IN AN AREA UTILIZING SOUND DETECTION AND COMPARISON

CROSS-REFERENCE TO RELATED APPLICATIONS

This application is related to and claims the benefit of Provisional U.S. patent application No. 60/820,311 filed by Farhan on Jul. 25, 2006 and incorporated herein by reference.

BACKGROUND OF THE INVENTION

The present invention relates to monitoring and reporting of activity based on actual detected sounds that are compared to expected or known sounds and, more particularly in one embodiment is directed towards a health or wellness monitoring system and apparatus, that detects sub-normal, abnormal and/or normal behavior of a person or object and reports it to a central database which in turn makes the information available to the family member or to the caregiver.

DESCRIPTION OF THE RELATED ART

Several patents and patent applications exist that are directed to methods and systems that detect motion of the individual rather than detecting routine activities through the use of audio. Such references that detect motion, either through motion or sound sensors, are functionally inadequate to perform the feature of using trend analysis to determine an abnormal condition presented herein. Occupant movement in the household may or may not directly correlate to proper or safe living conditions. One of the most reliable indications of proper and safe living conditions is to monitor for activities that an occupant would normally perform in order to maintain a safe and comfortable environment. Therefore, it may be more useful to detect an ancillary input, e.g. sound from daily activities, rather than a primary input, e.g. motion. To more fully illustrate the systems and methods of the prior art, we draw specific reference to U.S. Pat. No. 4,284,849 to Anderson et al. ("Anderson"), U.S. Patent Application Publ. No. 2002/0171551 A1 to Eshelman et al. ("Eshelman"), and U.S. Pat. No. 6,445,298 B1 to Shepher ("Shepher"). More specifically, Anderson teaches the use of sensors to detect and report the performance, or non-performance, of routine activities by the user. Sensors detect routine activities such as the opening or closing a refrigerator door, the exiting and leaving a bathroom, and the like. The activities are monitored and recorded on a daily basis, i.e. over a 24-hour period. If certain activities are not performed in 24 hours, an alarm is sent to a caregiver. Although Anderson arguably discloses a method and system to monitor a household for routine activities, Anderson fails to teach a method and system that is functionally similar to the various embodiments presented for the present invention. For instance, Anderson is more suitable to conditions that require instantaneous analysis, whereas embodiments of the present invention are more suitable to daily living. Further, Anderson does not teach the use of a programmable processor that takes as its primary input an audio detection device. Additionally, Anderson fails to teach the use of trend analysis as a means for detecting abnormal activity. Rather, Anderson, monitors activities on a daily basis. As an example of the arguable difference between the two inventions, while Anderson would be able to detect the use of a vacuum cleaner, it would be impractical to use Anderson to detect that the vacuum cleaner is being used infrequently and in fewer spaces (indicating a possible lowering of clean living conditions). Since an exemplary embodiment of the present invention uses trend analysis, this deviation, while completely transparent to the invention of Anderson, would be readily visible to embodiments of the present invention and would properly sound an alarm condition. Eshelman discloses a system that monitors a variety of independent signals and combines them to analyze for possible abnormal or emergency conditions. Eshelman does use an audio detector to detect for activities within a household (paragraph 63: . . . sound of . . . vacuum cleaner, etc.). However, Eshelman differs greatly from the disclosed embodiments in that the data is used in a dissimilar manner. Eshelman discloses the combination of multiple sensor inputs to generate one output. Because multiple inputs are used, and taking into account possible errors in the programming associated with those multiple inputs, the output of Eshelman may generate data not indicative of the actual conditions of the household. Further, Eshelman does not disclose the use of trend analysis to help in determining alarm or abnormal conditions. Finally, Shepher teaches a system and method for monitoring movement, wherein the movement is detected by infrared motion detectors or direction audio sensors. Because motion does not necessary correlate to normal or abnormal living conditions, Shepher does not solve the same disadvantages or shortcomings over the prior art that are resolved by the various embodiments of the present invention.

BRIEF SUMMARY OF THE INVENTION

According to one embodiment of the present invention, a device located near or within a substantially enclosed environment, similar to a household, will detect or listen to the non-speech sounds around and/or within the environment. The detected non-speech sounds are examined to identify sound patterns that have been previously recorded or 'learned', or otherwise created and made accessible for comparison purposes. Examples of these sounds include, but are not limited to the opening or closing of a refrigerator door, opening or closing a particular drawer, turning on of a light switch or an appliance, etc. The choice of which sound must be recorded and later detected is based on the habitual behavior of the person, animal, entity or object to be monitored. If the monitored entity has a particular routine, such as boiling water around seven in the morning to make instant coffee, then the sound of the kettle whistling would be a target sound for learning and subsequent detection. The requirement for these candidate sounds is that they have to sound similar to one another every time they are made. Examples of consistent sounds are the closing of a refrigerator door or a kettle whistling when the water inside comes to a boiling point. The present invention counts the number of occurrences of a particular sound in a particular time interval, such as a unit of sub-hour interval, and performs a comparison to a historical average for the same interval of time. A decision rule is then employed to determine below normal activity for the particular interval. The performance for each interval is then reported to a central database via a telephone line, a high speed internet uplink, or other communication technology which in turn is made available to a family member or a caregiver in a numerical and/or graphical fashion, or any other entity, device or individual that may be interested or have a reasonable reason for obtaining the information. For example, a security guard may receive reports of sounds in a guarded facility. A prison guard may receive reports regarding the sounds in the prison. A factory operator may receive sounds regarding the operation of machinery in the factory.

DETAILED DESCRIPTION OF THE INVENTION

Figure 1:
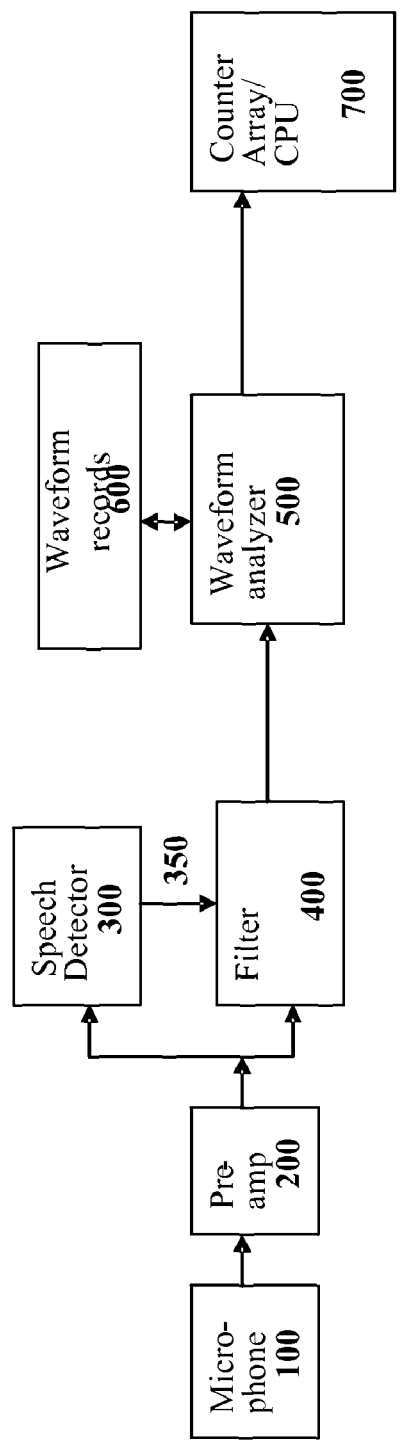
FIG. 1 is the top level block diagram of one embodiment of the invention showing the major functional blocks of the illustrated embodiment.

One embodiment of the present invention is a Wellness Monitoring system as illustrated in FIG. 1 for the purpose of detecting reoccurring non-speech sounds around a room representing habitual behavior of an individual. The sound energy is detected by microphone 100 and is fed to the 'Pre-Amp' 200. The output of the Pre-Amp 200 is a normalized digitized signal which is explained in FIG. 2 below and is simultaneously fed to a Speech Detector 300 and a 'filter' 400. The control signal 350 is used to signal the filter 400 when to pass the signal to the waveform analyzer block 500. The speech detector 300 is capable of detecting the presence of human voice (speech) and also can detect silence periods. The speech detector may also be programmed to detect other sounds that are of little to no interest, such as passing by automobiles, horn beeps, white noise generated by an air outlet of a heating and air conditioning unit, etc. Waveform Analyzer 500 takes non-speech signals between silence periods and with the control of the microprocessor (Central Processing Unit—CPU 640 shown in FIG. 4) running a software algorithm performs pattern matching to previously stored audio signals or Waveform records 600. The Counter array 700 is multi-dimensional array in software used to keep track of the occurrences of each recorded waveform for a selected period of time, such as a sub-hour interval as a non-limiting example, and over a course of an extended period of time, such as a twenty four hour period as a non-limiting example.

Figure 2:
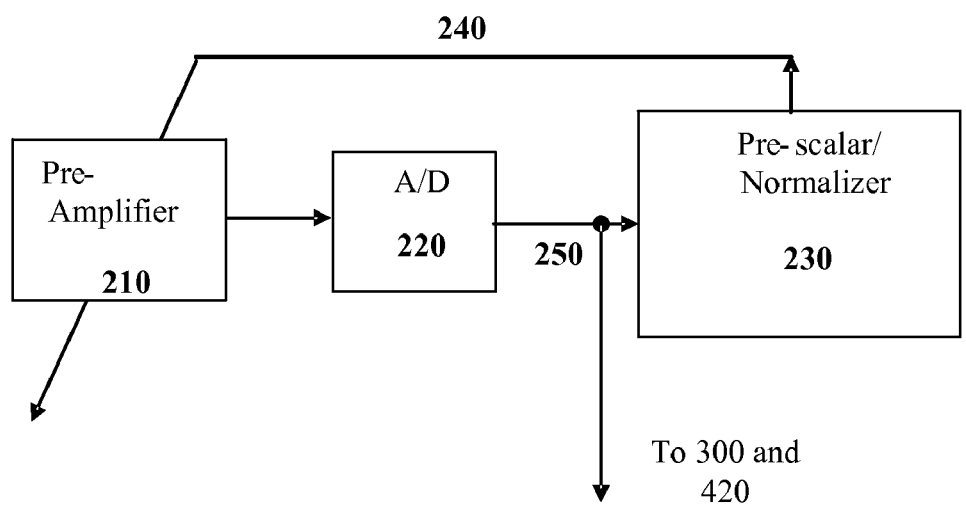
FIG. 2 is the exploded view of the 'Pre-Amp' block 200 which includes a Pre-amplifier an Analog-to-Digital converter and a pre-scalar/power normalizer.

The role of the Pre-Amp as shown in FIG. 2 is to convert the small signal received by the microphone to the level required by the Analog-to-Digital converter (A/D) 220. The pre-scalar 230 will normalize the digitized signal by adjusting the gain of the pre-amplifier 210 based on the peak power seen by 230 to maximize the dynamic range of 220 and prior to clipping.

Figure 3:
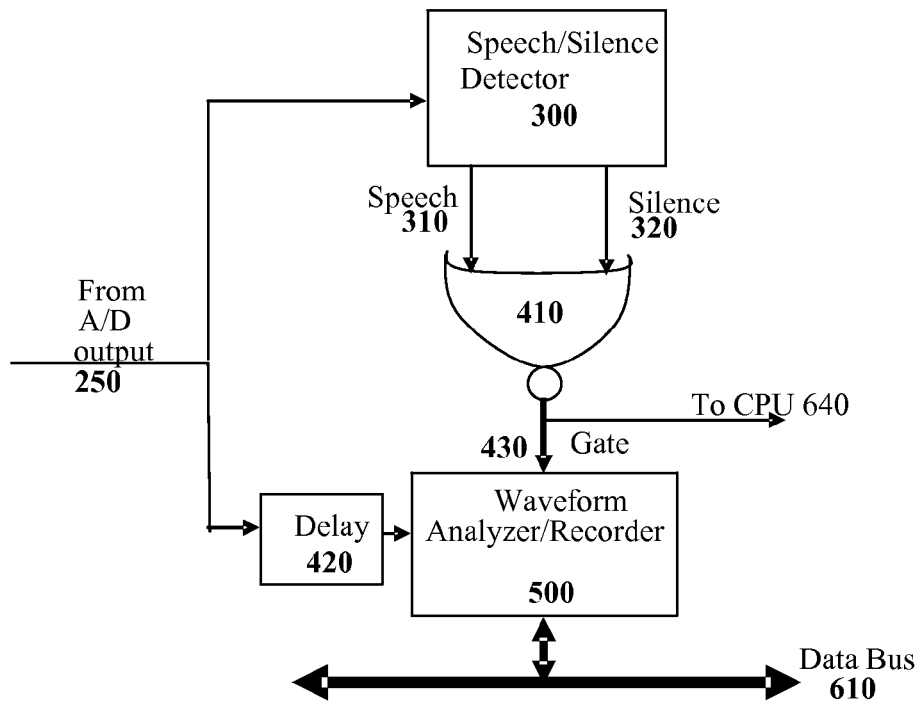
FIG. 3 is the exploded view of the of the 'Filter' block 400 wherein the details of the interface between the Speech detector/Silence detector and the waveform analyzer is shown.

FIG. 3 illustrates the details of the interface between the speech/silence detector 300 and the waveform analyzer/recorder 500. When the speech/silence detector 300 detects the presence of human speech (voice) it raises digital signal 310. When the speech/silence detector 300 detects silence, which is absence of any audio energy, then it raises digital signal 320. Block 420 is a digital delay block to apply an amount of delay equal to the processing delay of 300. The processing delay of 300 is the larger amount of time required by the speech/silence detector 300 to detect a valid voice digital signal 310 or a silence digital signal 320. For example, if the speech/silence detector 300 takes 10 milliseconds to detect speech and takes 2 milliseconds to detect silence then the amount of delay 420 will be 10 milliseconds worth of audio signal. Signals 310 and 320 are then fed to the input of a dual-input NOR gate. The output of the NOR gate is then fed to the "Gate" input 430 of block 500. So the input 430 of block 500 will only go high when neither a speech signal 310 nor a silence signal 320 is present. This is exactly when the signal needs to be analyzed. As soon as input 430 toggles (speech or silence is detected), the waveform recording stops and the analysis begins.

Figure 4:
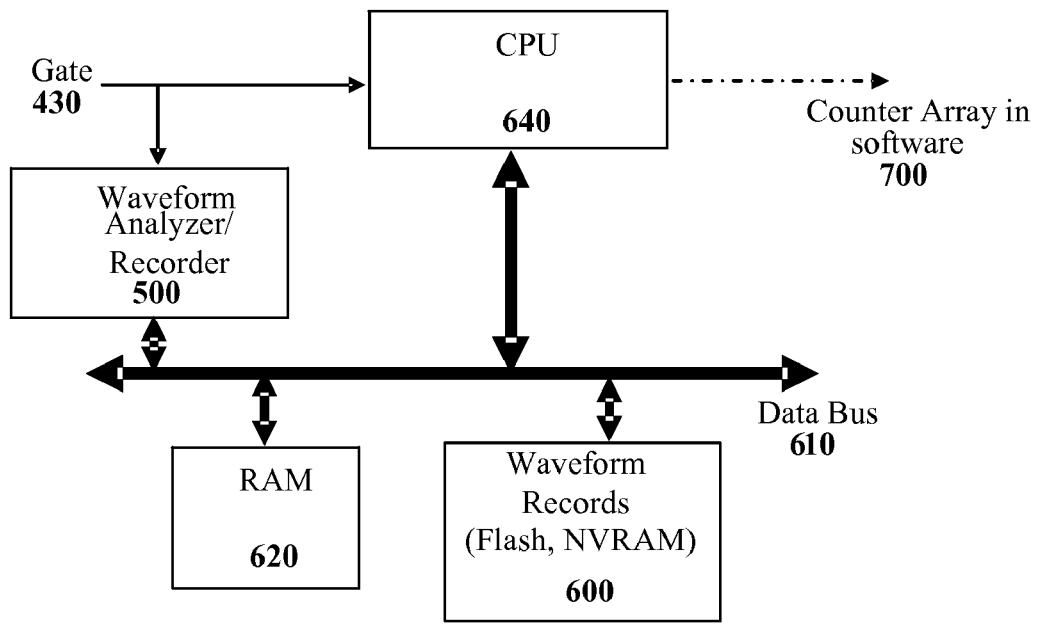
FIG. 4 is the exploded view of the 'Waveform Analyzer block 500.

In FIG. 4 the details of the waveform analysis is shown. The waveform recorder/analyzer block 500 acts as a buffer to store incoming non-speech audio waveforms between silence periods. The gate signal 430 is used to delineate the recording period. Once 430 toggles from high to low, the digital waveform is transferred to Random Access Memory (RAM) 620. Subsequently 500 becomes ready to receive the next non-speech audio waveform. Once in RAM, the CPU 640 will perform pattern matching algorithm, depicted in FIG. 5, to determine whether a recognizable audio pattern has been encountered. By use of RAM the CPU can perform the audio pattern recognition independent of the nature or rate of arrival of incoming audio patterns.

Figure 5:
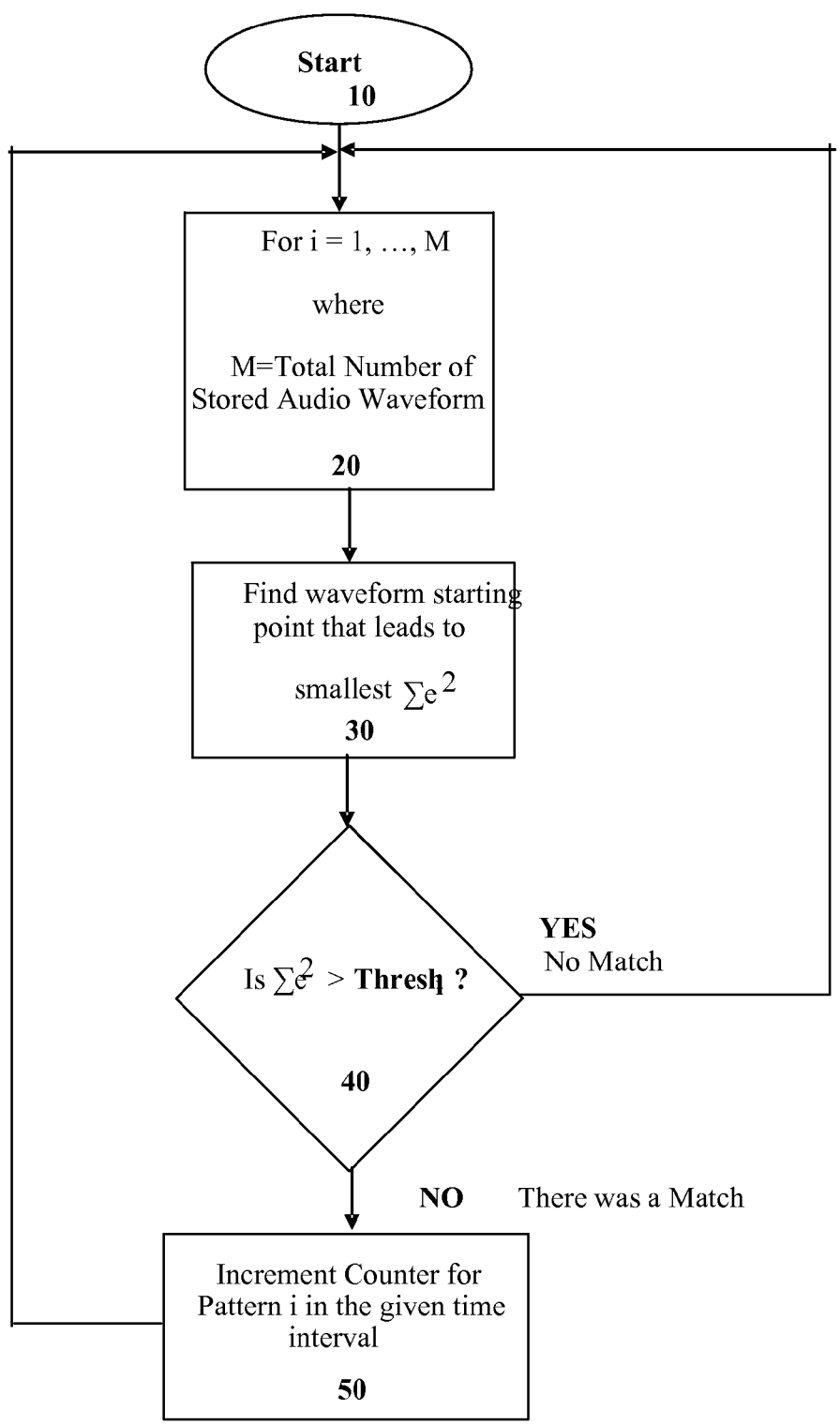
FIG. 5 is an illustration of the waveform pattern recognition algorithm.

The audio pattern recognition algorithm illustrated in FIG. 5 is one technique to perform the pattern recognition in various embodiment of the present invention and operates as follows. The process begins at point 10. There is a loop between 20 and 50 used to compare the incoming waveform to each and every type stored previously in non-volatile memory. Step 30 adjusts for the starting point of the incoming waveform that would lead to the smallest error squared summation. Error squared is defined as the difference between stored waveform and the incoming waveform squared or $e^2$ and error squared summation is $e^2$ computed over the entire span of the incoming waveform or also shown as $\Sigma e^2$. In step 40, $\Sigma e^2$ adjusted for optimal starting point is compared to a number $Thresh_i$, where $i=1, \ldots, M$ and M is the number of previously trained and stored waveforms. $Thresh_i$ is simply the average of at least three $\Sigma e^2$ computed for three occurrences of a desired audio sound. For example let us assume that the user has decided that the opening of the refrigerator door is a good indication of habitual behavior of his or her elderly relative, thus requiring it to be stored for subsequent detection. He will prepare the device for training by selecting the appropriate command in its menu. The user interface in one embodiment of the invention will instruct the user to push a button on the device and immediately open the refrigerator door. When the sounds ends, the user is instructed to indicate that recoding should stop. The device will accept this attempt as the base and instruct the user to repeat this cycle for at least two more times. Every time the cycle is repeated, the training waveform is committed to non-volatile (or permanent) memory and $\Sigma e^2$ is calculated. Subsequently an average of $\Sigma e^2$ is computed. The final average then is stored as $Thresh_i$. $Thresh_1$ is therefore the decision making threshold used for the first training sound waveform.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

It will be appreciated by persons skilled in the art that the present invention is not limited by what has been particularly shown and described herein above. Rather the scope of the invention is defined by the claims that follow.

What is claimed is:

1. A device for monitoring and detecting sounds to identify activity of a person in a substantially enclosed environment, the device comprising the components of:
   an audio receiver configured to:
      detect non-voice sounds within the substantially enclosed environment;
      in response to detecting non-voice sounds, begin to record the detected non-voice sounds;
      subsequent to detecting non-voice sounds, detect voice sounds or silence within the substantially enclosed environment;
      in response to detecting a voice sounds or silence, convert the non-voice sounds recorded prior to the detection of the voice sounds or silence into electronic signals;
   a speech processor for receiving the electronic signals and forming digital audio signals;
   a digital audio waveform analyzer operable to store digital audio waveforms and compare two or more digital audio waveforms to perform pattern recognition; and
   a processing unit operable to:
      place the digital audio waveform analyzer into a learning mode for receiving and storing digital audio waveforms for various sounds,
      place the digital audio waveform analyzer into a detecting mode for receiving digital audio waveforms and comparing them to previously recorded digital audio waveforms; and
      performing behavioral trend analysis of the noises in the substantially closed environment over a course of time.

2. The device of claim 1, wherein the processing unit is a software controllable processing unit.

3. The device of claim 1, wherein said waveform analyzer is capable of digitizing audio signals.

4. The device of claim 1, wherein said waveform analyzer is capable of comparing an audio pattern with a previously stored pattern after power normalizing the received waveform using pattern recognition techniques.

5. The device of claim 4, wherein the pattern recognition technique comprises root mean square calculations.

6. The device of claim 1, wherein said processor is capable of operating in a learning mode to store digitized audio signal for subsequent retrieval and comparison.

7. The device of claim 1, wherein said processor is operable to count the number of occurrences of matches to each uniquely stored audio pattern during a first period of time and retain the count for a second period of time.

8. The device of claim 7, wherein the first period is less than an hour and the second period is 24 hours.

9. The device of claim 7, wherein said processor is operable to perform trend analysis by comparing the match counts to monthly averages to determine, normal activity, below normal activity or zero activity and report back to a centralized server.

10. A method for detecting abnormal activity in an environment, the method comprising the steps of:
    recording sounds expected to occur in the environment;
    storing information representing each unique expected sound into a waveform record;
    an audio receiver recording non-voice sounds separated by silence or voice sounds occurring in the environment over a first period of time;
    a processor identifying each non-voice sound by comparing the non-voice sound to the stored information of unique expected sounds in the waveform record;
    the processor maintaining a count of the number of occurrences for each identified non-voice sound over the first period of time;
    the processor comparing the counts to expected values for each count within that first period of time;
    and
    the processing sounding an alarm condition based at least in parts on the counts and the expected values.

11. The method of claim 10, wherein the step of sounding an alarm further comprises the step of, if the maintained counts deviate from the expected counts by a threshold amount, reporting such information to a centralized server.

12. The method of claim 10, wherein the step of sounding an alarm further comprises the steps of:
    for each count, reporting (a) if the count exceeds the expected count by a first threshold amount, (b) is less than the expected count by a second threshold amount or (c) is within a threshold distance from the expected count.

* * * * *